United States Patent
Schroeder et al.

(10) Patent No.: US 9,585,938 B2
(45) Date of Patent: Mar. 7, 2017

(54) EGFR-BASED PEPTIDES

(75) Inventors: Joyce A. Schroeder, Tucson, AZ (US); Benjamin G. Bitler, Cheltenham, PA (US); Aarthi Goverdhan, Houston, TX (US)

(73) Assignee: ARIZONA CANCER THERAPEUTICS, LLC, Tuscon, AZ (US)

( * ) Notice: Subject to any disclaimer, the term of this patent is extended or adjusted under 35 U.S.C. 154(b) by 814 days.

(21) Appl. No.: 13/879,143

(22) PCT Filed: Oct. 12, 2011

(86) PCT No.: PCT/US2011/055894
§ 371 (c)(1),
(2), (4) Date: May 30, 2013

(87) PCT Pub. No.: WO2012/051247
PCT Pub. Date: Apr. 19, 2012

(65) Prior Publication Data
US 2013/0251727 A1   Sep. 26, 2013

Related U.S. Application Data

(60) Provisional application No. 61/392,249, filed on Oct. 12, 2010.

(51) Int. Cl.
*A61K 45/00* (2006.01)
*A61K 38/17* (2006.01)
(Continued)

(52) U.S. Cl.
CPC ............ *A61K 38/179* (2013.01); *A61K 45/06* (2013.01); *C07K 14/71* (2013.01); *A61K 38/00* (2013.01); *C07K 2319/10* (2013.01)

(58) Field of Classification Search
CPC ........ C07K 19/00; C07K 14/71; A61K 38/18; A61P 35/00
See application file for complete search history.

(56) References Cited

U.S. PATENT DOCUMENTS 7,767,642 B2   8/2010   Schroeder
8,093,208 B2   1/2012   Schroeder
(Continued)

FOREIGN PATENT DOCUMENTS

JP   2005510200   4/2005
JP   2008500815   1/2008
(Continued)

OTHER PUBLICATIONS

Extended European Search Report issued in related European Application No. 11833299.8, dated Mar. 28, 2014.
(Continued)

*Primary Examiner* — Cherie M Stanfield

(57) ABSTRACT

Observations regarding the role of MUC1 in promoting the nuclear accumulation of EGFR led us to propose the development of peptides to block nuclear accumulation of EGFR as a means to block breast cancer progression. One exemplary peptide, the ENLS1 peptide, promotes cell death in breast cancer cell lines. Studies in the MMTV-pyMT mouse model of breast cancer demonstrate significant anti-tumor activity.

1 Claim, 7 Drawing Sheets

(51) Int. Cl.
  C07K 14/71    (2006.01)
  A61K 45/06    (2006.01)
  A61K 38/00    (2006.01)

(56) References Cited

U.S. PATENT DOCUMENTS

| | | |
|---|---|---|
| 2005/0282744 A1 | 12/2005 | Hollingsworth |
| 2006/0293234 A1* | 12/2006 | Schroeder ............ C07K 14/005 424/1.69 |
| 2011/0014195 A1 | 1/2011 | Schroeder |

FOREIGN PATENT DOCUMENTS

| | | |
|---|---|---|
| JP | 2008503498 | 2/2008 |
| WO | WO 0034308 A2 * | 6/2000 |
| WO | 02058450 | 8/2002 |
| WO | 2004092339 | 10/2004 |
| WO | 2005042573 | 5/2005 |
| WO | 2005090407 | 9/2005 |
| WO | 2006002114 | 1/2006 |
| WO | 2006113667 | 10/2006 |
| WO | 2009105557 A1 | 8/2009 |
| WO | 2012051247 | 4/2012 |

OTHER PUBLICATIONS

Dittmann et al., "Nuclear EGFR shuttling induced by ionizing radiation is regulated by phosphorylation at residue Thr654," FEBS Letters, vol. 584, No. 18, Sep. 1, 2010, pp. 3878-3884.
Dietz et al., "Delivery of bioactive molecules into the cell: the Trojan horse approach," Molecular and Cellular Neurosciences, vol. 27, No. 2, Oct. 1, 2004, pp. 85-131.
USPTO; Final Office Action dated Jun. 25, 2015 in U.S. Appl. No. 12/867,396.
M.C. Berenbaum, "Synergy, additivism and antagonism in immunosuppresstion," Welcome Laboratories of Experimental Pathology, Variety Club Research Wing, St. Mary's Hospital Medical School, London, pp. 1-18, (1976).
Weisenthal, Human Tumor Assay Journal, on-line at http://weisenthal.org/synergy1.htm, 1 page, (2012).
JPO; Office Action dated Aug. 17, 2015 in Application No. 2014-174796.
AU; Notice of Acceptance dated Oct. 29, 2015 in Application No. 2011316653.
Bitler, B.G., et al., "Intracellular MUC1 Peptides Inhibit Cancer Progression," Clinical Cancer Research, vol. 15, pp. 100-109, (Dec. 31, 2008).
Bitler, B.G., et al., "MUC1 regulates nuclear localization and function of the epidermal growth factor receptor," Journal of Cell Science, vol. 123, pp. 1716-1723, (Apr. 20, 2010).
Bitler, B.G., "Determining the Role of MUC1 and Beta-Catenin on the Epidermal Growth Factor Receptor Signaling and Localization in Breast Cancer," The University of Arizona, pp. 1-183, (2010).
Katterle, Y., et al., "Antitumour effects of PLC-gamma1-(SH2)2-TAT fusion proteins on EGFR/c-erbB-2-positive breast cancer cells," British Journal of Cancer, vol. 90, pp. 230-235, (Jan. 12, 2004).
International Search Report Issued May 21, 2012 in PCT/US11/055894 Filed Oct. 12, 2011.
USPTO; Restriction Requirement dated May 29, 2008 in U.S. Appl. No. 11/404,959.
USPTO; Non-Final Office Action dated Aug. 20, 2008 in U.S. Appl. No. 11/404,959.
USPTO; Final Office Action dated Feb. 12, 2009 in U.S. Appl. No. 11/404,959.
USPTO; Restriction Requirement dated Dec. 18, 2009 in U.S. Appl. No. 11/404,959.
USPTO; Notice of Allowance dated May 25, 2010 in U.S. Appl. No. 11/404,959.
USPTO; Non-Final Office Action dated Feb. 24, 2011 in U.S. Appl. No. 12/847,355.
USPTO; Notice of Allowance dated Oct. 7, 2011 in U.S. Appl. No. 12/847,355.
USPTO; Restriction Requirement dated Jul. 25, 2012 in U.S. Appl. No. 12/867,396.
USPTO; Non Final Office Action dated Nov. 7, 2012 in U.S. Appl. No. 12/867,396.
USPTO; Final Office Action dated May 14, 2013 in U.S. Appl. No. 12/867,396.
USPTO; Non-Final Office Action dated Dec. 17, 2014 in U.S. Appl. No. 12/867,396.
PCT; International Search Report dated Aug. 29, 2006 in Application No. PCT/US2006/014485.
PCT; Written Opinion dated Aug. 29, 2006 in Application No. PCT/US2006/014485.
PCT; International Preliminary Report on Patentability dated Oct. 16, 2007 in Application No. PCT/US2006/014485.
PCT; International Search Report and Written Opinion dated May 8, 2009 in Application No. PCT/US2009/034541.
PCT; International Preliminary Report on Patentability dated Aug. 24, 2010 in Application No. PCT/US2009/034541.
PCT; International Search Report and Written Opinion dated May 21, 2012 in Application No. PCT/US2011/055894.
PCT; International Preliminary Report on Patentability dated Apr. 16, 2013 in Application No. PCT/US2011/055894.
AU; Examination Report dated Jul. 11, 2011 in Application No. 2006236441.
AU; Examination Report dated Jun. 19, 2013 in Application No. 2009215503.
CIPO; Office Action dated Sep. 5, 2012 in Application No. 2601823.
CIPO; Office Action dated May 21, 2013 in Application No. 2601823.
CN; Notification of First Office Action dated Sep. 21, 2010 in Application No. 200680011038.2.
CN; Notification of Second Office Action dated Feb. 18, 2011 in Application No. 200680011038.2.
CN; Notification of Third Office Action dated May 18, 2011 in Application No. 200680011038.2.
CN; Notification of Decision of Rejection dated Oct. 25, 2011 in Application No. 200680011038.2.
CN; Notification of Third Office Action dated Jul. 17, 2013 in Application No. 200680011038.2.
CN; Notification of First Office Action dated Jul. 9, 2012 in Application No. 200980109625.9.
CN; Notification of Second Office Action dated Mar. 12, 2013 in Application No. 200980109625.9.
CN; Notification of Third Office Action dated Nov. 19, 2013 in Application No. 200980109625.9.
EPO; European Search Report dated Jul. 31, 2009 in Application No. 06758384.9.
EPO; Office Action dated Jul. 7, 2011 in Application No. 06758384.9.
EPO; Office Action dated Jan. 30, 2013 in Application No. 06758384.9.
EPO; Office Action dated Jul. 9, 2013 in Application No. 06758384.9.
EPO; Office Action dated Sep. 19, 2012 in Application No. 09712807.8.
EPO; Office Action dated Jan. 30, 2013 in Application No. 09712807.8.
JPO; Office Action dated Sep. 7, 2011 in Application No. 2008-506817.
JPO; Office Action dated Jul. 8, 2013 in Application No. 2010-547751.
JPO; Office Action dated May 1, 2014 in Application No. 2010-547751.
JPO; Office Action dated Sep. 29, 2014 in Application No. 2013-533960.
Alpaugh, et al., "Cooperative Role of E-Cadherin and Sialyl-Lewis X/ A-Deficient MUC1 in the Passive Dissemination of Tumor Emboli in Inflammatory Breast Carcinoma," Oncogene, 21, pp. 3631-3643, (2002).

(56) References Cited

OTHER PUBLICATIONS

Alroy, et al., "The ErbB Signaling Network in Embryogenesis and Oncogenesis: Signal Diversification Through Combinatorial Ligand-Receptor Interactions," FEBS Letters, 410, pp. 83-86, (1997).
Anders, et al., "Understanding and Treating Triple-Negative Breast Cancer," Oncology (Williston Park), 22, pp. 1233-1240, and 1243, (2008).
Andersen, et al., "Kinetics and Equilibria in Ligand Binding by Nitrophorins 1-4: Evidence for Stabilization of a Nitric Oxide-Ferriheme Complex Through a Ligand-Induced Conformational Trap," Biochemistry, 39, pp. 10118-10131, (2000).
Andrechek, et al., "Tyrosine Kinase Signalling in Breast Cancer: Tyrosine Kinase-Mediated Signal Transduction in Transgenic Mouse Models of Human Breast Cancer," Breast Cancer Res. 2, pp. 211-216, (2000).
Bowie, et al., "Deciphering the Message in Protein Sequences: Tolerance to Amino Acid Substitutions," Science, 247, pp. 1306-1310, (1990).
Brossart, et al., "The Epithelial Tumor Antigen MUC1 is Expressed in Hematological Malignancies and is Recognized by MUC1-Specific Cytotoxic T-lymphocytes," Cancer Res., 61, pp. 6846-6850, (2001).
Brooks, et al., "Tat Peptide-Mediated Cellular Delivery: Back to Basics," Adv/ Drug Deliv. Rev., 57, pp. 559-577, (2005).
Carpenter, "The EGF Receptor: A Nexus for Trafficking and Signaling," Bioessays, 22, pp. 697-707, (2000).
Choi, et al., "Erlotinib Prevents Pulmonary Metastasis in Curatively Resected Breast Carcinoma Using a Mouse Model" Oncol. Rep., 16, pp. 119-122, (2006).
Console, et al., "Antennapedia and HIV Transactivator of Transcription (TAT) 'Protein Transduction Domains' Promote Endocytosis of High Molecular Weight Cargo Upon Binding to Cell Surface Glycosaminoglycans," J. Biol. Chem., 278, pp. 35109-35114, (2003).
Dassonville et al., "EGFR Targeting Therapies: Monoclonal Antibodies Versus Tyrosine Kinase Inhibitors: Similarities and Differences," Crit. Rev. Oncol./Hematol., 62, pp. 53-61, (2007).
Dawson, et al., "Three Distinct D-Amino Acid Substitutions Confer Potent Antiangiogenic Activity on an Inactive Peptide Derived from a Thrombospondin-1 Type 1 Repeat," Mol. Pharmacol., 55, pp. 332-338, (1999).
Finn, et al., "Estrogen Receptor, Progesterone Receptor, Human Epidermal Growth Factor Receptor 2 (HER2), and Epidermal Growth Factor Receptor Expression and Benefit from Lapatinib in a Randomized Trial of Paclitaxel With Lapatinib or Placebo as First-Line Treatment in HER2-Negative or Unknown Metastatic Breast Cancer," J. Clin. Oncol., 27, pp. 3908-3915, (2009).
Friess, et al., "Combination Treatment with Erlotinib and Pertuzumab Against Human Tumor Xenografts is Superior to Monotherapy," Clin. Cancer Res., 14, pp. 5300-5309, (2005).
Gottlieb, et al., "Natural Biology of Polyomavirus Middle T Antigen," Microbial Mol. Bio. Rev., 65, pp. 288-318; second and third pages, table of contents, (2001).
Green, et al., "Beta-Catenin Antisense Treatment Decreases Beta-Catenin Expression and Tumor Growth Rate in Colon Carcinoma Xenografts," J. Surgical Res., 101:1, pp. 16-20, (2001).
Guy, et al., "Induction of Mammary Tumors by Expression of Polyomavirus Middle T Oncogene: A Transgenic Mouse Model for Metastatic Disease," Mol. Cell. Biol., 12, pp. 954-961, (1992).
Guy, et al., "Expression of the Neu Protooncogene in the Mammary Epithelium of Transgenic Mice Induces Metastatic Disease," Proc. Natl. Acad. Sci. USA, 89, pp. 10578-10582, (1992).
Ha, et al., "Mechanism of Phosphorylation-Dependent Binding of APC to Beta-Catenin and its Role in Beta-Catenin Degradation," Mol. Cell, 15, pp. 511-521, (2004).
Hadzisejdic, et al., "Nuclear EGFR in Ductal Invasive Breast Cancer: Correlation with Cyclin-Dl and Prognosis," Mod. Pathol., 23, pp. 392-403, (2010).

Harada, et al., "Antitumor Protein Therapy; Application of the Protein Transduction Domain to the Development of a Protein Drug for Cancer Treatment," Breast Cancer, 13, pp. 16-26, (2006).
He, et al., "Identification of c-MYC as a Target of the APC Pathway," Science, 281, pp. 1509-1512, (1998).
Hilkens, et al., "Is Episialin/MUC1 Involved in Breast Cancer Progression?" Cancer Letters, 90, pp. 27-33, (1995).
Ho, et al., "Synthetic Protein Transduction Domains: Enhanced Transduction Potential in Vitro and in Vivo," Cancer Res., 61, pp. 474-477, (2001).
Hollingsworth, et al., "Mucins in Cancer: Protection and Control of the Cell Surface," Nat. Rev. Cancer, 4, pp. 45-60, (2004).
Hong, et al., "Isolation of a Peptide for Targeted Drug Delivery Into Human Head and Neck Solid Tumors," Cancer Res., 60, p. 6551-6556, (2000).
Hsu, et al., "Characterization of a Novel Tripartite Nuclear Localization Sequence in the EGFR Family," J. Biol. Chem., 282, pp. 10432-10440, (2007).
Huber, et al., "The Cadherin Cytoplasmic Domain is Unstructured in the Absence of Beta-Catenin. A possible Mechanism for Regulating Cadherin Turnover," J. Biol. Chem. 276, pp. 12301-12309, (2001).
Huber, et al., "The Structure of the Beta-Catenin/E-Cadherin Complex and the Molecular Basis of Diverse Ligand Recognition by Beta-Catenin," Cell, 5, pp. 391-402, (2001).
Jimenez, et al., "Signals Leading to Apoptosis-Dependent Inhibition of Neovascularization by Thrombospondin-1," Nat. Med., 6, pp. 41-48, (2000).
Kittiworakam, et al. "HIV-1 Tat Raises an Adjuvant-Free Humoral Immune Response Controlled by its Core Region and its Ability to Form Cysteine-Mediated Oligomers," J. Biol. Chem., 281, pp. 3105-3115, (2005).
Li, et al., "Interaction of Glycogen Synthase Kinase 3β with the DF3/MUC1 Carcinoma-Associated Antigen and β Catenin," Mol. Cell. Biol., pp. 7216-7224, (1998).
Li, et al., "The C-SRC Tyrosine Kinase Regulates Signaling of the Human DF3/MUC1 Carcinoma-Associated Antigen with GSK3 Beta and Beta-Catenin," J. Biol. Chem., 276, pp. 6061-6064, (2001).
Li, et al., "The Epidermal Growth Factor Receptor Regulates Interaction of the Human DF3/MUC1 Carcinoma Antigen with c-Src and Beta-Catenin," J. Biol. Chem., 276: 38, pp. 35239-35242, (2001).
Lilien, et al., "The Regulation of Cadherin-Mediated Adhesion by Tyrosine Phosphorylation/Dephosphorylation of Beta-Catenin," Curr. Opin. Cell. Biol., 7, pp. 459-465, (2005).
Lin, et al., "Progression to Malignancy in the Polyoma Middle T Oncoprotein Mouse Breast Cancer Model Provides a Reliable Model for Human Diseases," Am. J. Pathol., 163, pp. 2113-2126, (2003).
Lo, et al., "Nuclear-Cytoplasmic Transport of EGFR Involves Receptor Endocytosis, Importin Betal and CRM1," J. Cell. Biochem., 98, pp. 1570-1583, (2006).
Loftin, et al., "A Novel Copper-Binding Fold for the Periplasmic Copper Resistance Protein CusF," Biochemistry, 44, pp. 10533-10540, (2005).
Lopez, et al., "CD44 Attenuates Metastatic Invasion During Breast Cancer Progression," Cancer Res., 65, pp. 6755-6763, (2005).
MacDonald, et al., "Endostatin Binds Tropomyosin. A Potential Modulator of the Antitumor Activity of Endostatin," J. Biol. Chem. 276, pp. 25190-25196. (2001).
Madura, et al., "Activation of Pho in the Injured Axons Following Spinal Cord Injury," EMBO reports, 5, pp. 412-416, (2004).
Maes, et al., "Ultra High Resolution Structures of Nitrophorin 4: Heme Distortion in Ferrous CO and NO Complexes," Biochemistry 44, pp. 12690-12699, (2005).
Maglione, et al., "Transgenic Polyoma Middle-T Mice Model Premalignant Mammary Disease," Cancer Res., 61, pp. 8298-8305, (2001).
Michelson, et al. "Beta-Catenin is a Downstream Effector of Wnt-Mediated Tumorigenesis in the Mammary Gland," Oncogene, 20, pp. 5093-5099, (2001).

(56) References Cited

OTHER PUBLICATIONS

Morrison, et al., "Combinatorial Alanine-Scanning," Curr. Opin. Chem. Biol., 5, pp. 302-307, (2001).
Noguchi, et al., "Protein Transduction Technology: A Novel Therapeutic Perspective," Acta Medical Okayama, 60, pp. 1-11, (2006).
Olayioye, et al., "ErbB-1 and ErbB-2 Acquire Distinct Signaling Properties Dependent Upon Their Dimerization Partner," Mol. Cell. Biol., 18, pp. 5042-5051, (1998).
Olayioye, et al., "ErbB Receptor-Induced Activation of Stat Transcription Factors is Mediated by Src Tyrosine Kinases," J. Biol. Chem., 274, pp. 17209-17218, (1999).
Packer, et al., "Expression of the Cell Surface Mucin Gene Family in Adenocarcinomas," Int. J. Oncol., 25, pp. 1119-1126, (2004).
Parker, et al., "Distant Metastasis in Breast Cancer: Molecular Mechanisms and Therapeutic Targets," Cancer Bio. Ther., 2, pp. 14-21, (2003).
Piedra, et al., "Regulation of Beta-Catenin Structure and Activity by Tyrosine Phosphorylation," J. Biol. Chem., 276, pp. 20436-20443, (2001).
Pintens, et al., "Triple Negative Breast Cancer a Study from the Point of View of Basal CK5/6 and HER-1," J. Clin. Pathol., 62, pp. 624-628, (2009).
Pochampalli, et al., "MUC1 is a Novel Regulator of ErbB1 Receptor Trafficking," Oncogene, 26, pp. 1693-1701, (2007).
Pochampalli, et al., "Transforming Growth Factor Alpha Dependent Cancer Progression is Modulated by Muc1," Cancer Res., 67, pp. 6591-6598, (2007).
Polakis, P., "Wnt Signaling and Cancer," Genes Dev., 14, pp. 1837-1851, (2000).
Price, et al., "Tumorigenicity and Metastasis of Human Breast Carcinoma Cell Lines in Nude Mice," Cancer Res., 50, pp. 717-721, (1990).
Ren, et al., "Human MUC1 Carcinoma-Associated Protein Confers Resistance to Genotoxic Anticancer Agents," Cancer Cell, 5: pp. 163-175, (2004).
Roberts, et al. "Crystal Structure and Electron Transfer Kinetics of CueO, a Multicopper Oxidase Required for Copper Homeostasis in *Escherichia coli*," Proc. Natl. Acad. Sci. USA, 99, pp. 2766-2771, (2002).
Schneider, et al., "Protein Evolution: Structure-Function Relationships of the Oncogene Beta-Catenin in the Evolution of Multicellular Animals," J. Exp. Zool. Mol. Dev. Evol., pp. 295, 25-44, (2003).
Schroeder, et al., "MUC1 Alters Beta-Catenin-Dependent Tumor and Promotes Cellular Invasion," Oncogene, 22, pp. 1324-1332, (2003).
Schroeder, et al., "MUC1 Overexpression Results in Mammary Gland Tumorigenesis and Prolonged Alveolar Differentiation," Oncogene 23: pp. 5739-5747, (2004).
Schroeder, et al., "Dynamic Expression and Activation of ERBB Receptors in the Developing Mouse Mammary Gland," Cell Growth Differ., 9, 451-464, (1998).
Schroeder, et al., "Transgenic Mice Reveal Roles for TGFalpha and EGF Receptor in Mammary Gland Development and Neoplasia," J. Mammary Gland Biol. Neoplasia, 2, pp. 119-129, (1997).
Schroeder, et al., "Transgenic MUC1 Interacts With Epidermal Growth Factor Receptor and Correlates with Mitogen-Activated Protein Kinase Activation in the Mouse Mammary Gland," J. Biol. Chem., 276, pp. 13057-13064, (2001).
Schroeder, et al., "Cooperative Induction of Mammary Tumorigenesis by TGFalpha and Wnts," Oncogene, 19, pp. 3193-3199, (2000).
Schroeder, et al., "ErbB-Beta-Catenin Complexes are Associated with Human Infiltrating Ductal Breast and Murine Mammary Tumor Virus (MMTV)-Wnt-1 and MMTV-c-Neu Transgenic Carcinomas," J. Biol. Chem, 277, pp. 22692-22698, (2002).
Schwarze, et al., "Protein Transduction: Unrestricted Delivery into All Cells?" Trends Cell Biol., 10, pp. 290-295, (2000).
Schwarze, et al., "In Vivo Protein Transduction: Delivery of a Biologically Active Protein Into the Mouse," Science, 285: 5433, pp. 1569-1572, (1999).
Shutman, et al., "The Cyclin D1 Gene is a Target of the Beta-Catenin/LEF-1 Pathway," Proc. Natl. Acad. Sci. USA, 96, pp. 5522-5527, (1999).
Snyder, et al., "Cell Penetrating Peptides in Drug Delivery," Pharm. Res., 21, pp. 389-393, (2004).
Spicer, et al., "Delayed Mammary Tumor Progression in Muc-1 Null Mice," J. Biol. Chem., 270, pp. 30093-30101, (1995).
Spicer, et al., "Analysis of Mammalian MUC1 Genes Reveals Potential Functionally Important Domains," Mammalian Genome, 6, pp. 885-888, (1995).
Takahashi, et al., "Expression of MUC1 on Myeloma Cells and Induction of HLA Unrestricted CTL Against MUC1 from a Multiple Myeloma Patient," J. Immunol., 153, pp. 2102-2109, (1994).
Teruya-Feldstein, et al., "MUC-1 Mucin Protein Expression in B-Cell Lymphomas," Appl. Immunohistochem.. Mol. Morphol., 11, pp. 28-32, (2003).
Tetsu et al., "Beta-Catenin Regulates Expression of Cyclin D1 in Colon Carcinoma Cells," Nature, 398: 6726, pp. 422-426, (1999).
Trivedi, et al., "Augmentation of Leukocyte Infiltration in Murine Tumors Expressing B-Cell Derived but not Nasopharyngeal Carcinoma Derived EBV Membrane Protein LMP1," J. Med. Virol., 60, pp. 417-424, (2000).
Tsukamoto, et al., "Expression of the Int-1 Gene in Transgenic Mice is Associated with Mammary Gland Hyperplasia and Adenocarcinomas in Male and Female Mice," Cell, 55, pp. 619-625, 1988).
Wadia, et al., "Transducible TAT-HA Fusogenic Peptide Enhances Escape of TAT-Fusion Proteins After Lipid Raft Macropinocytosis," Nat. Med., 10, pp. 310-315, (2004).
Wadia, et al., "Transmembrane Delivery of Protein and Peptide Drugs by TAT-Mediated Transduction in the Treatment of Cancer," Adv. Drug Deliv. Rev., 57:4, pp. 579-596, (2005).
Webster, et al., "Requirement for Both Shc and Phosphatidylinositol 3' Kinase Signaling Pathways in Polyomavirus Middle T-Mediated Mammary Tumorigenesis," Mol. Cell. Biol. 18, pp. 2344-2359, (1998).
Weichsel, et al., "Nitric Oxide Binding to Nitrophorin 4 Induces Complete Distal Pocket Burial," Nat. Struct. Biol., 7, pp. 551-554, (2000).
Weichsel, et al., "Heme-Assisted S-Nitrosation of a Proximal Thiolate in a Nitric Oxide Transport Protein," Proc. Natl. Acad. Sci. USA, 102, pp. 594-599, (2005).
Weisenthal, "Synergy Analysis of Classic and Newer Drug Combinations," Human Tumor Assay J., www.weisenthal.org/synergy1, (2012).
White, et al., "Targeted Disruption of Beta1-Integrin in a Transgenic Mouse Model of Human Breast Cancer Reveals an Essential Role in Mammary Tumor Induction," Cancer Cell, 6, pp. 159-170, (2004).
Xing, et al., "Crystal Structure of a Beta-Catenin/Axin Complex Suggests a Mechanism for the Beta-Catenin Destruction Complex," Genes Dev., 17, pp. 2753-2764, (2003).
Yamamoto, et al., "Interaction of the DF3/MUC1 Breast Carcinoma-Associated Antigen and Beta-Catenin in Cell Adhesion," J. Biol. Chem., 272:19, pp. 12492-12494, (1997).
Zotter, et al., "Tissue and Tumor Distribution of Human Polymorphic Epithelial Mucin," Cancer Rev., 11-12, pp. 55-101, (1988).
Zrihan-Licht et al., "Tyrosine Phosphorylation of the MUC1 Breast Cancer Membrane Proteins. Cytokine Receptor-Like Molecules," FEBS Lett., 356, pp. 130-136, (1994).
Principles of Cancer Therapy: Merck Manual Professional, Chapter 149, Section 11, (2005).
Gefitinib-MeSH-NCBI, www.ncbi.nlm.nih.gov/mesh?term=gefitinib, (2012).
AU; Examination Report dated Jan. 8, 2015 in Application No. 2011316653.
CIPO; Office Action dated Jan. 29, 2015 in Application No. 2714939.

(56) References Cited

OTHER PUBLICATIONS

Lazar et al., "Transforming Growth Factor: Mutation of Aspartic Acid 47 and Leucine 48 Results in Different Biological Activities," Mol. Cell. Bio., 8, pp. 1247-1252, (1988).

* cited by examiner

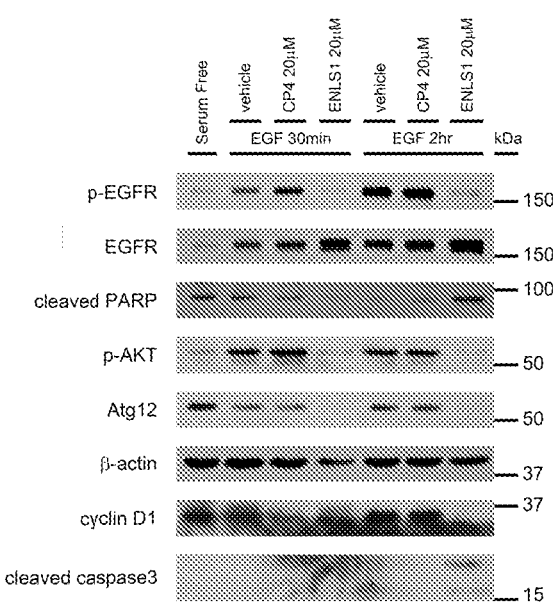 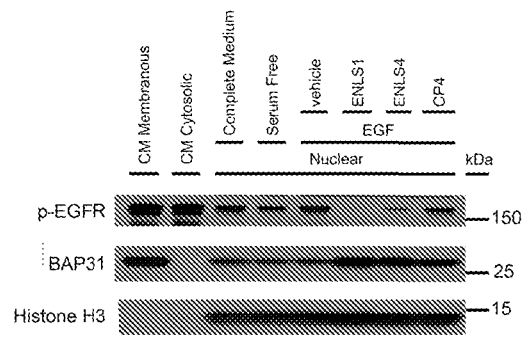
Fig. 4A                    Fig. 4B

Fig. 6A
Fig. 6B
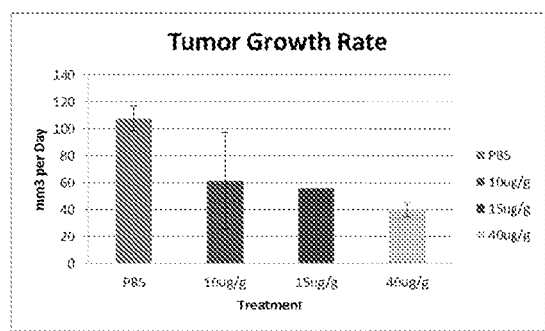
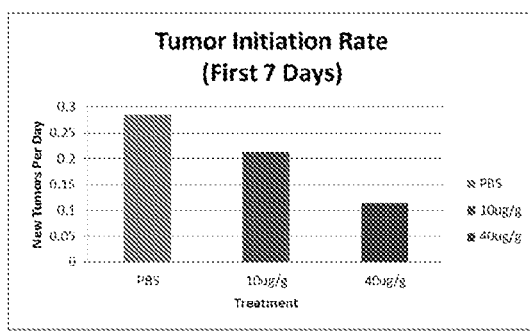
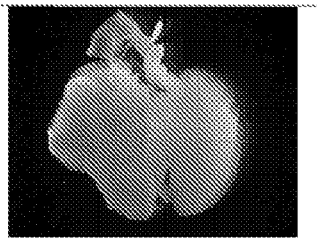
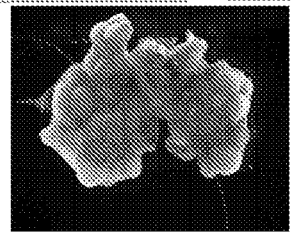
Fig. 6C
Fig. 6D

SEQUENCE LISTING

```
<160> NUMBER OF SEQ ID NOS: 22

<210> SEQ ID NO 1
<211> LENGTH: 13
<212> TYPE: PRT
<213> ORGANISM: Homo sapiens

<400> SEQUENCE: 1

Arg Arg Arg His Ile Val Arg Lys Arg Thr Leu Arg Arg
1               5                   10

<210> SEQ ID NO 2
<211> LENGTH: 11
<212> TYPE: PRT
<213> ORGANISM: Mus musculus

<400> SEQUENCE: 2

Tyr Ala Arg Ala Ala Ala Arg Gln Ala Arg Ala
1               5                   10

<210> SEQ ID NO 3
<211> LENGTH: 21
<212> TYPE: PRT
<213> ORGANISM: Homo sapiens

<400> SEQUENCE: 3

Phe Met Arg Arg Arg His Ile Val Arg Lys Arg Thr Leu Arg Arg Leu
1               5                   10                  15

Leu Gln Glu Arg Glu
            20

<210> SEQ ID NO 4
<211> LENGTH: 40
<212> TYPE: PRT
<213> ORGANISM: Homo sapiens

<400> SEQUENCE: 4

Leu Leu Leu Val Val Ala Leu Gly Ile Gly Leu Phe Met Arg Arg Arg
1               5                   10                  15

His Ile Val Arg Lys Arg Thr Leu Arg Arg Leu Leu Gln Glu Arg Glu
            20                  25                  30

Leu Val Glu Pro Leu Thr Pro Ser
        35                  40
```

-continued

<210> SEQ ID NO 5
<211> LENGTH: 14
<212> TYPE: PRT
<213> ORGANISM: Human immunodeficiency virus

<400> SEQUENCE: 5

Ser Gly Tyr Gly Arg Lys Lys Arg Arg Gln Arg Arg Arg Cys
1               5                   10

<210> SEQ ID NO 6
<211> LENGTH: 19
<212> TYPE: PRT
<213> ORGANISM: Drosophila melanogaster

<400> SEQUENCE: 6

Ser Gly Arg Gln Ile Lys Ile Trp Phe Gln Asn Arg Arg Met Lys Trp
1               5                   10                  15

Lys Lys Cys

<210> SEQ ID NO 7
<211> LENGTH: 34
<212> TYPE: PRT
<213> ORGANISM: Herpes simplex virus

<400> SEQUENCE: 7

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 8
<211> LENGTH: 32
<212> TYPE: PRT
<213> ORGANISM: Artificial Sequence
<220> FEATURE:
<223> OTHER INFORMATION: chimeric therapeutic peptide

<400> SEQUENCE: 8

Tyr Ala Arg Ala Ala Ala Arg Gln Ala Arg Ala Phe Met Arg Arg Arg
1               5                   10                  15

His Ile Val Arg Lys Arg Thr Leu Arg Arg Leu Leu Gln Glu Arg Glu
            20                  25                  30

<210> SEQ ID NO 9
<211> LENGTH: 21
<212> TYPE: PRT
<213> ORGANISM: Artificial Sequence
<220> FEATURE:
<223> OTHER INFORMATION: therapeutic peptide

<400> SEQUENCE: 9

Phe Met Arg Arg Arg His Ile Val Arg Lys Arg Thr Leu Arg Arg Leu
1               5                   10                  15

Leu Gln Glu Arg Glu
            20

<210> SEQ ID NO 10
<211> LENGTH: 13
<212> TYPE: PRT
<213> ORGANISM: Artificial Sequence
<220> FEATURE:

<223> OTHER INFORMATION: therapeutic peptide

<400> SEQUENCE: 10

Phe Met Arg Arg Arg His Ile Val Arg Lys Arg Thr Leu
1               5                   10

<210> SEQ ID NO 11
<211> LENGTH: 15
<212> TYPE: PRT
<213> ORGANISM: Artificial Sequence
<220> FEATURE:
<223> OTHER INFORMATION: therapeutic peptide

<400> SEQUENCE: 11

Ile Val Arg Lys Arg Thr Leu Arg Arg Leu Leu Gln Glu Arg Glu
1               5                   10                  15

<210> SEQ ID NO 12
<211> LENGTH: 13
<212> TYPE: PRT
<213> ORGANISM: Artificial Sequence
<220> FEATURE:
<223> OTHER INFORMATION: therapeutic peptide

<400> SEQUENCE: 12

Arg Arg Arg His Ile Val Arg Lys Arg Thr Leu Arg Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: therapeutic peptide

<400> SEQUENCE: 13

Arg Thr Leu Arg Arg Leu Leu Gln Glu Arg Glu
1               5                   10

<210> SEQ ID NO 14
<211> LENGTH: 12
<212> TYPE: PRT
<213> ORGANISM: Artificial Sequence
<220> FEATURE:
<223> OTHER INFORMATION: therapeutic peptide

<400> SEQUENCE: 14

Leu Leu Gln Glu Arg Glu Leu Val Glu Pro Leu Thr
1               5                   10

<210> SEQ ID NO 15
<211> LENGTH: 12
<212> TYPE: PRT
<213> ORGANISM: Artificial Sequence
<220> FEATURE:
<223> OTHER INFORMATION: therapeutic peptide

<400> SEQUENCE: 15

Ala Ala Gln Glu Arg Glu Ala Ala Glu Pro Leu Thr
1               5                   10

<210> SEQ ID NO 16
<211> LENGTH: 21
<212> TYPE: PRT
<213> ORGANISM: Artificial Sequence
<220> FEATURE:
<223> OTHER INFORMATION: therapeutic peptide

<400> SEQUENCE: 16

Phe Arg Met His Arg Ile Arg Val Arg Thr Lys Leu Arg Leu Arg Leu
1               5                   10                  15

Arg Gln Glu Arg Glu
            20

<210> SEQ ID NO 17
<211> LENGTH: 21
<212> TYPE: PRT
<213> ORGANISM: Artificial Sequence
<220> FEATURE:
<223> OTHER INFORMATION: therapeutic peptide

<400> SEQUENCE: 17

Phe Met Ala Ala Ala His Ile Val Ala Ala Ala Thr Leu Ala Ala Leu
1               5                   10                  15

Leu Gln Glu Arg Glu
            20

<210> SEQ ID NO 18
<211> LENGTH: 13
<212> TYPE: PRT
<213> ORGANISM: Artificial Sequence
<220> FEATURE:
<223> OTHER INFORMATION: therapeutic peptide

<400> SEQUENCE: 18

Phe Arg Met His Arg Ile Arg Val Arg Thr Lys Leu Arg
1               5                   10

<210> SEQ ID NO 19
<211> LENGTH: 15
<212> TYPE: PRT
<213> ORGANISM: Artificial Sequence
<220> FEATURE:
<223> OTHER INFORMATION: therapeutic peptide

<400> SEQUENCE: 19

Ile Val Arg Thr Lys Leu Arg Leu Arg Leu Arg Gln Glu Arg Glu
1               5                   10                  15

<210> SEQ ID NO 20
<211> LENGTH: 13
<212> TYPE: PRT
<213> ORGANISM: Artificial Sequence
<220> FEATURE:
<223> OTHER INFORMATION: therapeutic peptide

<400> SEQUENCE: 20

Arg Asp Arg His Ile Val Arg Asp Arg Thr Leu Arg Asp
1               5                   10

<210> SEQ ID NO 21
<211> LENGTH: 21
<212> TYPE: PRT
<213> ORGANISM: Artificial Sequence
<220> FEATURE:
<223> OTHER INFORMATION: therapeutic peptide

<400> SEQUENCE: 21

Phe Met Arg Asp Arg His Ile Val Arg Asp Arg Thr Leu Arg Asp Leu
1               5                   10                  15

Leu Gln Glu Arg Glu
            20

```
<210> SEQ ID NO 22
<211> LENGTH: 21
<212> TYPE: PRT
<213> ORGANISM: Artificial Sequence
<220> FEATURE:
<223> OTHER INFORMATION: therapeutic peptide

<400> SEQUENCE: 22

Phe Met Arg Gln Arg His Ile Val Arg Gln Arg Thr Leu Arg Gln Leu
 1               5                  10                  15

Leu Gln Glu Arg Glu
            20
```

EGFR-BASED PEPTIDES

TECHNICAL FIELD OF THE INVENTION

This invention is related to the area of cancer. In particular, it relates to anti-cancer peptides which inhibit growth and promote apoptosis.

BACKGROUND OF THE INVENTION

MUC1 and EGFR have each been shown to play roles in the growth and progression of cancers. Recent work has demonstrated a role for MUC1 in promoting EGFR activity in the nucleus. This nuclear translocation results in EGFR/chromatin interactions at the Cyclin D1 promoter, resulting in an increase in Cyclin D-1 expression (Bitler et al., 2010b).

There is a continuing need in the art to find effective ways to prevent the initiation of tumors, to inhibit the growth of cancer cells, to kill cancer cells, and to prevent metastasis of tumors.

SUMMARY OF THE INVENTION

According to one aspect of the invention a polypeptide comprises a nuclear translocation sequence of EGFR and a protein transduction domain which enhances translocation of attached macromolecules across cellular membranes.

According to another aspect of the invention a polypeptide comprises (a) human EGFR amino acid residues 622-642 as shown in SEQ ID NO: 3; (b) a permutation of residues 622-642 as shown in SEQ ID NO: 3; or (c) a variant of SEQ ID NO: 3 having from one to three arginine and/or lysine residues substituted with a glutamine residue; and a protein transduction domain which enhances translocation of attached macromolecules across cellular membranes.

Another aspect of the invention is a method. A polypeptide is administered to a mammal. The mammal has a breast tumor, or the mammal is predisposed to breast cancer, or the mammal has had a breast tumor resected. The polypeptide comprises (a) human EGFR amino acid residues 622-642 as shown in SEQ ID NO: 3; (b) a permutation of residues 622-642 as shown in SEQ ID NO: 3; (c) a variant of SEQ ID NO: 3 having from one to three arginine and/or lysine residues substituted with a glutamine residue; or (d) a nuclear translocation sequence of EGFR. The polypeptide also comprises a protein transduction domain which enhances translocation of attached macromolecules across cellular membranes.

According to another aspect another method is provided. A polypeptide is administered to a mammal. The mammal has a tumor, or the mammal is predisposed to developing a tumor, or the mammal has had a tumor resected. The tumor is selected from the group consisting of ovarian, colon, lung, prostate, or pancreatic tumors. The polypeptide comprises (a) human EGFR amino acid residues 622-642 as shown in SEQ ID NO: 3; (b) a permutation of residues 622-642 as shown in SEQ ID NO: 3; (c) a variant of SEQ ID NO: 3 having from one to three arginine and/or lysine residues substituted with a glutamine residue; or (d) a nuclear translocation sequence of EGFR. The polypeptide also comprises a protein transduction domain which enhances translocation of attached macromolecules across cellular membranes.

According to another aspect of the invention a method of treating a cancer cell is provided. The cancer cell is contacted with a polypeptide. The polypeptide comprises (a) human EGFR amino acid residues 622-642 as shown in SEQ ID NO: 3; (b) a permutation of residues 622-642 as shown in SEQ ID NO: 3; (c) a variant of SEQ ID NO: 3 having from one to three arginine and/or lysine residues substituted with a glutamine residue; or (d) a nuclear translocation sequence of EGFR. The polypeptide also comprises a protein transduction domain which enhances translocation of attached macromolecules across cellular membranes.

Another aspect of the invention is a method of treating an animal tumor model. A polypeptide is administered to the animal tumor model. The polypeptide comprises (a) human EGFR amino acid residues 622-642 as shown in SEQ ID NO: 3; (b) a permutation of residues 622-642 as shown in SEQ ID NO: 3; (c) a variant of SEQ ID NO: 3 having from one to three arginine and/or lysine residues substituted with a glutamine residue; or (d) a nuclear translocation sequence of EGFR. The polypeptide also comprises a protein transduction domain which enhances translocation of attached macromolecules across cellular membranes.

These and other aspects which will be apparent to those of skill in the art upon reading the specification provide the art with compositions and methods for inhibiting cancer cell growth and killing cancer cells.

BRIEF DESCRIPTION OF THE DRAWINGS

FIG. 1A. Sequence for the ENLS-1 peptide (SEQ ID NO: 8) and the PTD4 protein transduction domain (SEQ ID NO: 2). BT-20 breast cancer cells were treated on alternate days for 7 days with 1 uM, 10 uM, 50 uM or 100 uM of ENLS-1, or no peptide treatment (NT) and an MT assay was performed to quantify cell number. *, P=0.001; **, P<0.001, ANOVA. FIG. 1B. MDA-MB-231 breast cancer cells were treated with either 1, 5, 50, or 100 uM ENLS-1 or control PTD4 peptide, as indicated, for either 90 minutes or 48 hours, as indicated.

FIG. 4A-4B. ENLS1 treatment reduces pEGFR levels and induces apoptosis. MDA-MB-468 cells were treated with ENLS1, control peptide (CP4) or PBS, followed by treatment with EGF (10 ng/ml) for either 30' or 2 hours. FIG. 4A. Cell lysates were evaluated for expression of phosphorylated EGFR (which detects phosphor-845 EGFR), phosphorylated AKT, cyclin D1 and Atg12, a marker of autophagy. Cell lysates were also evaluated for induction of apoptosis, as measured by an induction of cleaved PARP and cleaved caspase-3. Protein loading was normalized by beta-actin expression. FIG. 4B. Cells were further fractionated to evaluate localization of phosphor-EGFR, with membrane, cytoplasmic and nuclear fractions shown. Fraction purity was evaluated by BAP31, a membrane protein and Histone H3, a nuclear protein. Molecular weights for all proteins are shown at the right.

FIG. 6A-6D. Tumor growth rate, initiation and metastasis is inhibited by ENLS1 treatment. MMTV-pyMT mice with at least 0.5 cm established tumors in at least one mammary gland were treated daily (1/day, 5 days/week×3 weeks) with the indicated doses of ENLS1/g body weight. In the case of the 40 ug/g body weight, mice were given ENLS1 2×/day for 8 days. FIG. 6A. tumor growth rate was determined by measuring the total tumor burden in all 10 mammary glands at the end of the treatment/total tumor burden in all 10 mammary glands at the beginning of treatment. FIG. 6B. Initiation of new tumors during the first 7 days of treatment was also determined by counting the number of new 0.5 cm tumors that formed during the course of treatment/number of days. A significant diminution of lung metastasis was also observed, with 2/9 treated mice developing visible lung mets (FIG. 6C) while 5/5 PBS treated mice developed lung metastases (FIG. 6D).

DETAILED DESCRIPTION OF THE INVENTION

Figure 1A:
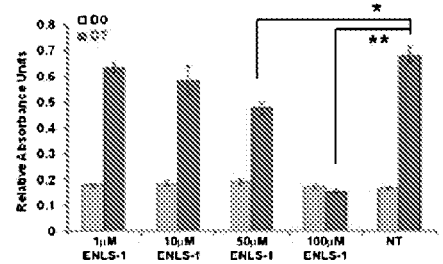
FIG. 1A-1B. ENLS1 peptide promotes cell death in triple-negative breast cancer cells.

The inventors have discovered that EGFR-related peptides, designed based on the EGFR juxtamembrane region, can be used to block the nuclear translocation of EGFR. The peptides include the tri-partite nuclear localization sequence of EGFR, which can act in a dominant-negative fashion to block nuclear translocation of EGFR. An EGFR peptide is fused to or synthesized in tandem with a protein transduction domain (e.g., PTD-4) to permit cellular uptake and intracellular action. One such peptide (dubbed ENLS1) has been tested for its ability to block breast cancer cell growth and tumor growth in a transgenic mouse model, MMTV-pyMT. Other peptides also have been tested and found to have cell growth inhibitory properties.

The EGFR portion of the peptides can be based on the following sequence from EGFR: LLLVVALGIGLFM RRRHIVRKRTLRRLLQERELVEPLTPS (SEQ ID NO: 4). This sequence is juxtamembrane in the cytoplasmic domain of EGFR. The tri-partite sequence (underlined) interacts with importin-1β and is required for EGFR nuclear localization (Hsu and Hung, 2007; Lo et al., 2006). A portion of this sequence is linked to a protein transduction domain (such as PTD4 previously described by Bitler et al., 2009). The linkage can be direct or through a linker. Linkers can be, for example, runs of a single amino acid, or may be alternating runs of two amino acids. Linkers can be, for example, from 1 to 25 residues in length. One polypeptide, dubbed ENLS1, has the following sequence: YARAAARQARAFMRRRHIVRKRTLRRLLQERE (SEQ ID NO: 8); the underlined sequence is PTD4 domain). This 32-mer peptide was made by synthesis; it is highly water soluble and stable for >1 week at 4° C. It can also be made by other techniques, including in recombinant cells. Recombinant cells can be formed, for example, by transforming or transfecting cells with a recombinant vector which encodes for a polypeptide as described, operably linked to a transcription initiation site.

The polypeptides of the invention do not occur in nature, but rather are made to juxtapose, a protein transduction domain with a sequence for blocking nuclear translocation of EGFR. The two sequences can be made to immediately abut one another or can be separated by a linker. The blocking sequence does not comprise all of EGFR, but instead comprises a subset of the EGFR amino acid sequence. Typically the size of the EGFR sequence will be less than 50 residues, less than 40, residues, less than 30 residues, or less than 25 residues. Smaller sequences may also be used, provided that they inhibit the nuclear translocation of endogenous EGFR. The nuclear translocation sequence may require one, two, or three of the arginine rich motifs, RRR, RKR, or RR, with or without the adjacent sequences in EGFR. Typically, the nuclear translocation sequence will be at least 6, at least 8, at least 10, at least 12, at least 14, at least 16, at least 18, at least 20 residues in length. Interestingly, permutations of the EGFR amino acid sequence also have inhibitory properties, thus the sequence of the residues is not an essential feature of the cancer cell inhibitory or apoptotic activity.

The protein transduction domain that is fused or linked to the EGFR portion may comprise any protein transduction domain that is known in the art. These include without limitation PTD-4, HSV type I protein VP22, and Antenapedia protein transduction domain (Antp). Protein transduction domains enhance cellular entry of macromolecules. The domains may be natural or synthetic.

Spacers for use in fusion proteins may be additional amino acid residues that are used in fusion proteins typically to facilitate manufacture or synthesis. These can be fairly innocuous and typically are of a length of from 1 to 5 residues. The linkers can be monotonous or mixed residue. The residues can be random or sequences obtained from other proteins or designed for a particular property, e.g., physical, chemical or biological. In one aspect, spacers provide an optimum distance between the two portions of the fusion protein.

The polypeptides may be formulated in any suitable vehicle for administration. Aqueous solutions may be used, but other alternatives may also be convenient, including capsules, time-release, implants, impregnated polymers, hydrophobic preparations, solids, powders, etc. The polypeptides can be combined with other anti-tumor agents, particularly with EGFR inhibitors. The polypeptides can be administered by any means known in the art, including but not limited to intravenous injection, intramuscular injection, intratumoral injection, oral, subcutaneous injection, and intralymphatic.

Cancers and cancer cells which may be treated include breast, skin, colon, ovarian, prostate, cervical, colorectal, lung, brain, head and neck, pancreatic, kidney, and liver. One effect which may be observed upon administration is a reduced extent or retarded rate of initiation, growth, invasion, and metastasis. Suitable assays for measuring these processes are described in the examples. Other assays as are known in the art can be used as well.

A person who is identified as having inherited genes associated with cancer is at increased risk of developing cancer. Such persons can be treated to reduce their risk of cancer initiation. Similarly, those who have been exposed to environmental risks, such as atomic bomb fall-out, nuclear fuel waste, and other pollutants, are at increased risk of developing cancer. Genes which may be mutated and the autosomal dominant disorders they cause include, but are not limited to BRCA1: breast cancer, BRCA2: breast cancer, APC: colon cancer HNPCC: colon cancer, CDKN2: melanoma. Other autosomal dominant inherited cancer risks include basal cell nevus syndrome, neurofibromatosis type 2, Carney syndrome, osteochondromatosis, multiple, chordoma, familial, paraganglioma, familial, Cowden syndrome, Peutz-Jeghers syndrome, esophageal cancer with tylosis, prostate cancer, gastric cancer, familial, renal cancer, familial, Li-Fraumeni syndrome, retinoblastoma, multiple endocrine neoplasia type 1, tuberous sclerosis, multiple endocrine neoplasia type 2, von Hippel-Lindau disease, neurofibromatosis type 1, and Wilms' tumor. Autosomal recessive disorders disposing to cancer include ataxia-telangiectasia Rothmund-Thomson syndrome, Bloom syndrome xeroderma pigmentosa, Werner's syndrome, and Fanconi's anemia.

EGFR inhibitors may be administered in the same treatment or prophylactic regimen as the peptides of the invention. They may be administered mixed with the peptides, or may be administered within a short time period of each other, such as within a week, within a day, or within a few hours or minutes. Thus combinations of the inhibitors and the peptides may be formed ex vivo during manufacturing and formulation or in vivo subsequent to administration to a mammal. The two agents may be combined in a package, i.e., a divided container to form a kit. Any EGFR inhibitor may be used, including kinase inhibitors. Exemplary but not exhaustive, the list of inhibitors may include panitumumab, cetuximab, gefitinib, and erlotinib.

The polypeptides may be useful in treatment, prevention, or adjuvant therapies. These words do not imply any particular level of cure or efficacy. Rather, any time that a polypeptide is applied to a cell, tissue, or mammal so that a biological effect can be observed, a treatment has occurred. Since no treatment is successful on all members of a particular disease population, it is only necessary that the treatment have an effect on a useful percentage of the population. Prescreening and assessments may be performed to ascertain those individuals who will be most likely to benefit from the polypeptides of the invention. These will include those with a tumor such as a breast, brain, ovarian, colon, or pancreatic tumor. These tumors often contain altered EGFR expression. Other disease or predispositions can be assessed by determining the presence of an EGFR mutation in a germline or somatic tissue of an individual. Alternatively a biopsy tissue may be tested to determine the efficacy or likely efficacy of the polypeptide for that particular individual. Family history of tumors may also be used as an indication that treatment may be beneficial. Exposure to carcinogens may be used as an indication that treatment may be beneficial.

Animal models of various cancers and other diseases may be used to assess the effect of the polypeptides with other agents. Combined additive or combined synergistic effects may be determined in animal models. Cellular models and tissue models may also be used, typically in advance of animal models or clinical testing.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Activity Against Cancer Cell Line

We first evaluated the ability of ENLS1 to inhibit the growth of breast cancer cell lines in culture. For these studies, we evaluated the effects of ENLS1 on the growth of MDA-MB-231, and BT20, both of which are positive for EGFR expression and have a basal-like phenotype. We found ENLS1 to have not only a strong anti-growth phenotype, but also a very potent killing phenotype. Treatment of triple-negative breast cancer cells (both BT20 and MDA-MB-231) results in an induction of cell death as measured by MTT assay (FIG. 1A).

Example 2

Activity in Mouse Model

Figure 2:
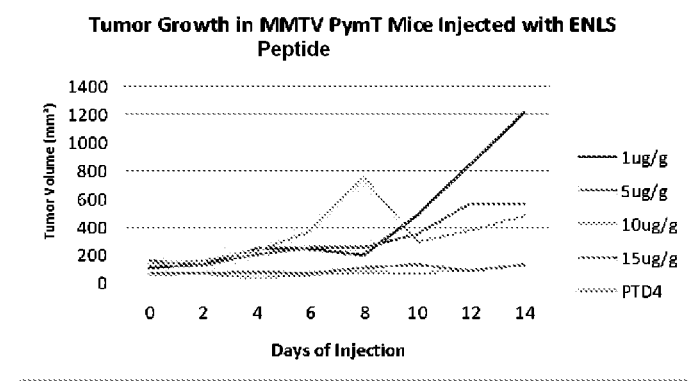
FIG. 2 ENLS1 inhibits tumor growth in the MMTV-pyMT mouse model. MMTV-pyMT mice were allowed to develop tumors of ~100 mm$^3$ in at least one mammary gland. This was followed by once daily injection (i.p.) of the indicated concentration of ENLS-1 for [(5 days)×3]. Tumor volumes indicate the total tumor volume/mouse.

We have also determined that ENLS1 can block tumor growth in the MMTV-pyMT transgenic mouse model of breast cancer. We chose this model as it has been previously demonstrated to be an excellent model for human breast cancer (Lin et al., 2003). Furthermore, its initiation is not dependent on EGFR activity, and is therefore an excellent model of spontaneous disease (Andrechek and Muller, 2000). We began treatment of tumor bearing MMTV-pyMT mice with 25 ug/g body weight ENLS1, but this treatment was met with pulmonary toxicity (data not shown). We next began treatment of tumor bearing MMTV-pyMT mice with 1 ug/g body weight ENLS1, and this treatment gave no observable toxicities. Based on this lack of toxicity, we began increasing the dosage of ENLS1 to 5 ug/g body weight, followed by 10 and 15 ug/g body weight. We did not see any apparent toxicity at any of these doses. We observed significant anti-tumor effects at both 10 and 15 ug/g body weight dosages, compared to either the lower concentration doses or a PTD4 control injection (FIG. 2). In both of these cases, we observed no significant growth of tumors in these mice, evaluating growth of tumors in 10 glands in each case. These results indicate that ENLS1 has potent anti-tumor activity in the MMTV-pyMT mouse model of breast cancer.

Example 3

EGFR Juxtamembrane Peptides Kill Breast Cancer Cells

We have evaluated the efficacy of 14 different drugs for their ability to inhibit the growth of triple negative breast cancers. We have identified one of these drugs (ENLS1), containing hEGFR$^{622-42}$, that effectively blocks tumor cell growth in both in vitro cell growth assays and in an established mouse model of breast cancer. We investigated the mechanism of action for this drug and found that it induces apoptosis, accompanied by membrane blebbing and reduction of nuclear localization of erbB1. Sequence identity indicates a block of erbB1, erbB2 and erbB3 nuclear translocation.

Recent data from our lab has demonstrated a prominent role for MUC 1 in promoting the nuclear activity of erbB receptors in driving transformation (Bitler et al., Journal of Cell Science, 2010). Given this activity, we focused on blocking nuclear localization of erbB receptors and MUC1 for developing anti-tumor peptides. The erbB receptors have significant homology in the nuclear localization sequence, all bearing a tri-partite basic amino acid sequence in their juxtamembrane region. In addition, a 3 residue basic sequence in the juxtamembrane of MUC1 has also been shown to drive nuclear localization of MUC1. We therefore designed peptides around this region of EGFR, and those sequences are as shown in Table 1.

ENLS1 effectively blocks cell growth in 2 different pancreatic cell lines (BxPC3 and AsPc1) as well as HER2 positive T47D breast cancer cells. It had no effect, though, on HEK293 cells, which do not express the HER receptors (data not shown).

TABLE 1

| | Name | Sequence | Change | Day 3 Survival | SEQ ID NO: |
|---|---|---|---|---|---|
| hEGFR$^{622-42}$ | ENLS-1 | PTD4-FMRRRHIVRKRTLRRLLQERE | | 5% | 9 |
| hEGFR$^{622-34}$ | ENLS-2 | PTD4-FMRRRHIVRKRTL········ | -RRLLQERE | 73% | 10 |
| hEGFR$^{628-42}$ | ENLS-3 | PTD4-·······IVRKRTLRRLLQERE | FMRRRH- | 37% | 11 |
| hEGFR$^{624-36}$ | ENLS-4 | PTD4-···RRRHIVRKRTLRR······ | FM--LLQERE | 78% | 12 |
| hEGFR$^{632-42}$ | ENLS-5 | PTD4-··········RTLRRLLQERE | FMRRRHIVRK- | 62% | 13 |
| hEGFR$^{637-48}$ | EBL-1 | PTD4-··············LLQERELVEPLT | Basolateral Domain | 96% | 14 |
| hEGFR$^{637-48LV\Delta4\times A}$ | cEBL-1 | PTD4-··············AAQEREAAEPLT | EBL-1 L and V to A | 98% | 15 |
| hEGFR$^{s622-42}$ | nlsCPv1 | PTD4-FRMHRIRVRTKLRLRLRQERE | Scramble ENLS-1 | 5% | 16 |
| hEGFR$^{622-42RK\Delta8\times A}$ | nlsCPv2 | PTD4-FMAAAHIVAAATLAALLQERE | A for R and K | Not Sol. | 17 |
| hEGFR$^{s622-34}$ | cENLS-2 | PTD4-FRMHRIRVRTKLR········ | Scramble ENLS-2 | 83% | 18 |
| hEGFR$^{s628-42}$ | cENLS-3 | PTD4-·······IVRTKLRLRLRQERE | Scramble ENLS-3 | 51% | 19 |
| hEGFR$^{624-36RK\Delta3\times D}$ | nlsCPv4 | PTD4-···RDRHIVRDRTLRD······ | ENLS-4 R to D | 99% | 20 21 |
| hEGFR$^{622-42RK\Delta3\times D}$ | nlsCPv5 | PTD4-FMRDRHIVRDRTLRDLLQERE | ENLS-1 R to D | 100% | 22 |
| hEGFR$^{622-42RK\Delta3\times Q}$ | nlsCPv6 | PTD4-FMRQRHIVRQRTLRQLLQERE | ENLS-1 R to Q | 35% | 23 |

Figure 1B:
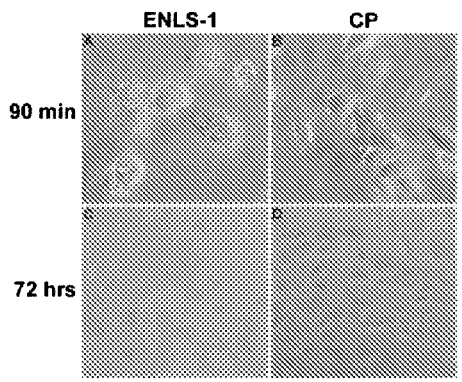

We next evaluated the ability of each of these peptides to inhibit the growth of the triple-negative breast cancer line, MDA-MB-468. In our previous studies, we had demonstrated that these cells were particularly sensitive to a loss of MUC1 expression for nuclear-EGFR-dependent effects, including Cyclin D1 expression. Cells were evaluated for effects of peptide on growth inhibition by MTT assay at 1, 3 and 5 days of 20 uM peptide treatment. Peptide concentration is based on evaluations of the ability of the peptide to block cell growth at 0.1 uM-100 uM concentrations, where 20 uM was found to optimally reduce cell growth in the active peptide, without any effects in the control peptide (data not shown). We then treated MDA-MB-468 cells with 14 derivatives of the peptide, including versions with the full sequence, portions of the sequence, and acidic substitutions for the basic amino acids (which were synthesized as controls) (Table 1). We found that a key 21 amino acid sequence is optimal for causing cell death, which is encompassed by ENLS1 (FIG. 1). In addition, while data shown is for MDA-MB-468 cells, growth inhibitory effects were observed for MDA-MB-231 and BT20 cells as well (both triple negative breast cancers).

We then proceeded to evaluate cell death in other cell types, including HER2 and HER3 positive cells, and HER negative cells. In addition, we evaluated the efficacy of ENLS1 on pancreatic cells. Surprisingly, we found that

Example 4

ENLS1-Dependent Cell Death is Via Apoptosis

We next set out to determine whether cell death was occurring by the induction of apoptosis. For this, we treated cells for either 30 minutes or 2 hours and made protein lysates (FIG. 2a). Lysates were then analyzed by SDS-PAGE and immunoblot for expression of cleaved caspase 3 and cleaved PARP, both markers of the induction of apoptosis. We found that by 2 hours of peptide treatment, both were induced, indicating that cells were dying by apoptosis. In addition, we found that these cancer cells had established a state of autophagy for survival (as demonstrated by expression of atg12). ENLS1 was also observed to block the formation of atg12, indicating a loss of the cell preserving the autophagic state. No effects on protein expression for any proteins evaluated were affected by our control peptide. In addition, we observed a loss of Cyclin D1 expression, which is known to be induced by nuclear EGFR. Finally, we found a loss of pAKT expression, which we subsequently found to correlate with a loss of total AKT expression. We are currently evaluating the mechanism by which this may be occurring.

We next set out to verify that we are blocking the nuclear translocation of EGFR, which we evaluated by fractionating the cytoplasmic, membrane and nuclear fraction of cells treated with ENLS1 versus ENLSCP5 (the control peptide with 3 key amino acids changed from basic (arginine) to acidic (aspartic acid). In FIG. 2b, we demonstrate that while EGFR is phosphorylated on residue 845 (p-EGFR) in response to EGF treatment, this form of EGFR does not translocate to the nucleus in the presence of ENLS1, whereas it readily translocates to the nucleus in the control (either vehicle or CP4 control peptide). ENLS4 also inhibits the nuclear translocation of p-EGFR, as ENLS4 is the minimal nuclear translocation sequence of EGFR. Interestingly, ENLS4 has minimal effects on cell growth (FIG. 1), indicating that the loss of EGFR translocation can inhibit cell growth, but that another function must be being affected by ENLS1.

Example 5

ENLS1 Treatment Induces Vesicle Formation in Cells

Figure 3:
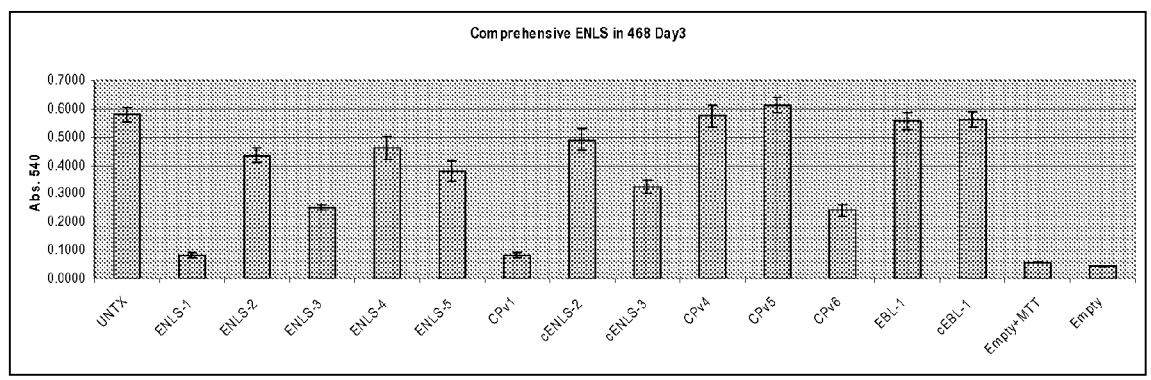
FIG. 3. Nuclear localization sequence of EGFR can serve as a dominant block to cell growth. MDA-MB-468 cells were grown for 3 days in the presence of the peptide indicated (sequence is shown in Table 1). At the end of 3 days, an MTT assay was performed to measure cell growth.

To determine how ENLS1 was driving the cells to undergo apoptosis, we began by evaluating the morphological changes that are observed upon ENLS1 treatment. We noticed that within a few hours of peptide treatment, cells began to exhibit membrane blebbing, demonstrating a membrane 'bubbling' (data not shown). We decided to look by electron microscopy to determine what changes were occurring at a sub-structural level. Upon performance of scanning electron microscopy, we were able to identify the formation of multiple vesicles under the plasma membrane of ENLS1 treated cells, but not in control-treated cells (FIG. 3). We are currently investigating the origin of these vesicles through investigations into membrane integrity, calcium flux and exocytosis in the cell.

Example 6

ENLS1 Inhibits Tumor Growth and Metastasis in the MMTV-pyMT Mouse Model of Breast Cancer We have been extensively testing the ability of ENLS1 to affect breast cancer growth in vivo. We have been testing the MMTV-pyMT model of breast cancer, a model that forms spontaneous breast tumors in all 10 mammary glands of the mouse. This model has been extensively evaluated by pathologists, and shown to undergo many of the same changes that occur in human breast cancer. In addition this is a metastatic model, with metastases forming in the lung in close to 100% of the animals.

MMTV-pyMT mice were allowed to develop tumors of at least 0.5 cm in diameter prior to treatment, and were then treated for 15 days with either 1 ug/g body weight (n=1), 5 ug/g body weight (n=1), 10 ug/g body weight (n=4), 15 ug/g body weight (n=1), or 40 ug/g body weight (n=1). This was done initially to determine if treatment with ENLS1 would result in toxicity. We found that no toxicity to the animal (as determined by evaluated changes in weight, grooming, gait) was observed at any of the treatment groups. We next began to evaluate the effects of peptide treatment on tumor growth. The MMTV-pyMT model is a stochastically developing tumor model, with tumors developing in all ten mammary glands from as early as 6 weeks of age. This allows us to determine both how drug treatment effects established tumors as well as newly initiated tumors. FIG. 4a shows that ENLS1 exhibits strong antitumor activity, as shown by the tumor growth rate in the animals treated, also that this effect on tumor growth increases as the amount of drug increases. In FIG. 4b, we demonstrate that ENLS1 treatment inhibits the initiation of new tumors during the treatment. Finally, we found a striking reduction in lung metastases in treated mice versus control mice. This model is known to be 100% metastatic to the lungs, and we therefore excised the lungs of untreated and control mice to evaluate effects of ENLS1 on lung metastasis. We found only 2/9 mice that had been treated with ENLS1 with visible lung metastases, while all of the control mice (5/5) had lung metastases.

Example 7

Inhibition of Tumor Growth in the MMTV-pyMT Model is Associated with Apoptosis

Figure 5:
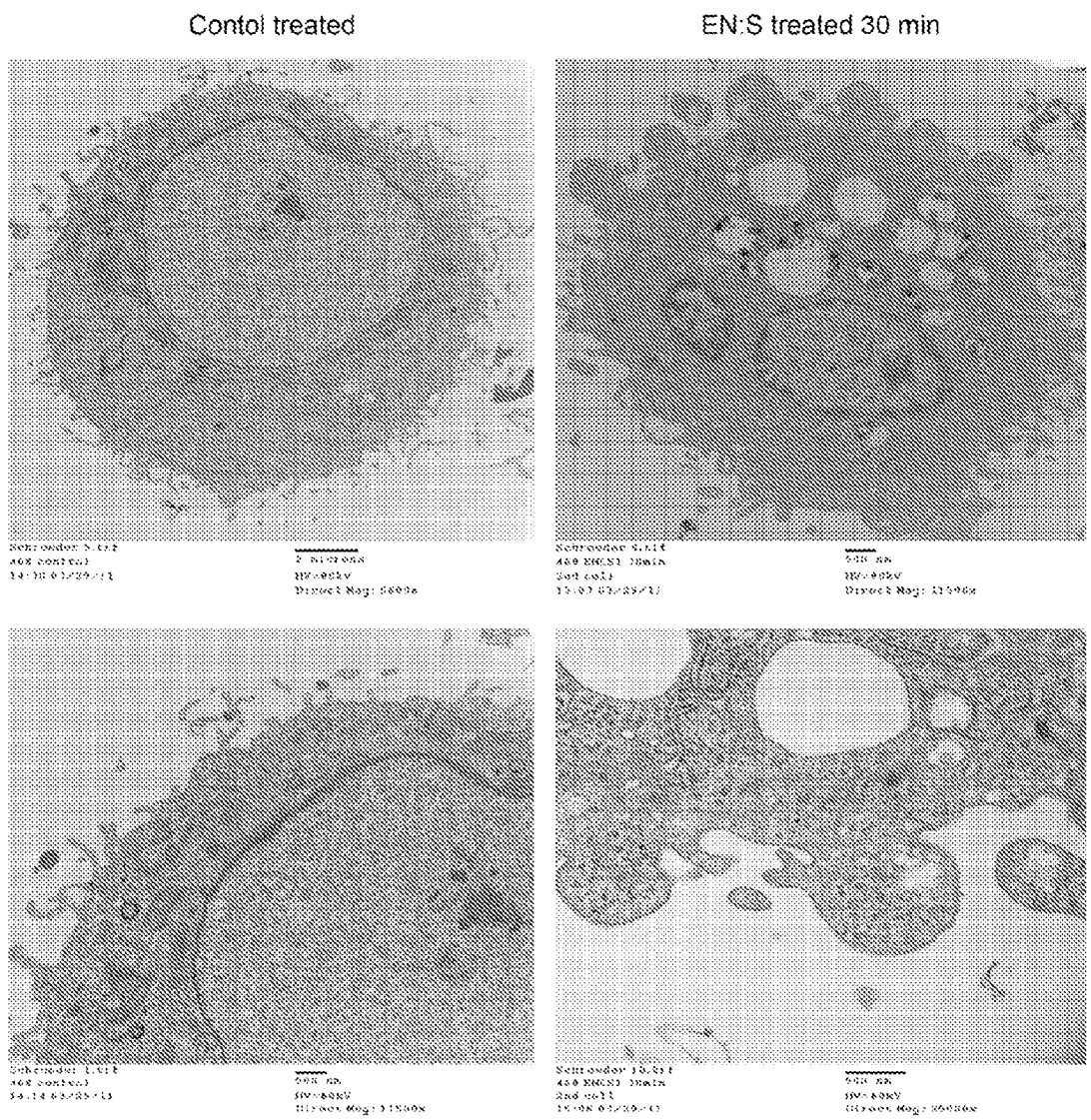
FIG. 5. Vesicle formation occurs in ENLS1-treated cells. MDA-MB-468 cells were treated with either control peptide or ENLS1 for 30 minutes, fixed, sectioned and visualized by electron microscopy.
Figure 7:
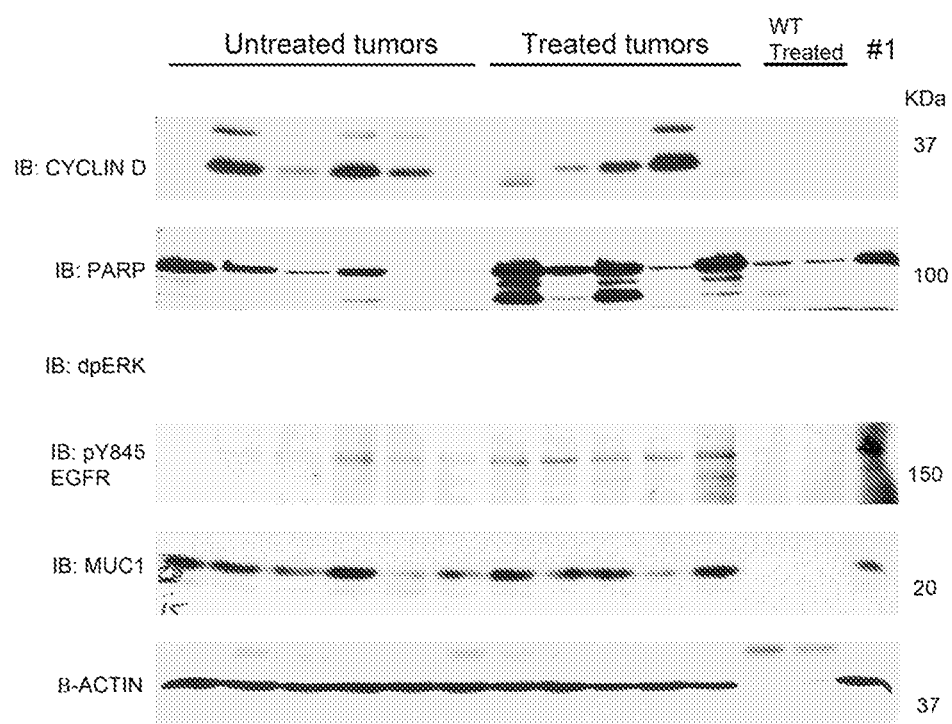
FIG. 7. MMTV-pyMT mice treated with ENLS1 have tumors with increased cleavage of PARP. At the end of 15 days of treatment (1×/day, intraperitoneal injection, [daily× 5]×3), mice were sacrificed and remaining tumors were homogenized in protein lysis buffer. Proteins were separated by SDS-PAGE, and evaluated by immunoblot for expression of cyclin D1, cleaved PARP, phosph-EGFR (at residue 845), MUC1 and beta-actin (loading control). Molecular weights are shown at the right, and 5 tumor lysates are shown for both untreated and ENLS1 treated mice, as well as 2 non-tumor bearing wildtype animals.

Finally, we have evaluated the molecular events occurring in the tumors excised from treated mice. Mice that had received 10 ug/g body weight of ENLS1 for 15 days were sacrificed and protein lysates prepared from the remaining tumors. We then evaluated these protein lysates for expression of cleaved PARP as an indicator of the induction of apoptosis, and found a significant increase in cleaved PARP in ENLS1 treated tumors (FIG. 5). We also evaluated tumors for the expression of Cyclin D1, pY845EGFR, and MUC1, but did not observe any significant differences.

REFERENCES

The disclosure of each reference cited is expressly incorporated herein.

Anders, C., and Carey, L. A. (2008). Understanding and treating triple-negative breast cancer. Oncology (Williston Park) 22, 1233-1239; discussion 1239-1240, 1243.

Andrechek, E. R., and Muller, W. J. (2000). Tyrosine kinase signalling in breast cancer: tyrosine kinase-mediated signal transduction in transgenic mouse models of human breast cancer. Breast Cancer Res 2, 211-216.

Bitler, B. G., Goverdhan, A., and Schroeder, J. A. (2010a). MUC1 Regulates Nuclear Localization and Function of the Epidermal Growth Factor Receptor. Journal of Cell Science, 2010 May 15; 123:1716-23. Epub 2010 Apr. 20

Bitler, B. G., Goverdhan, A., and Schroeder, J. A. (2010b). MUC1 regulates nuclear localization and function of the epidermal growth factor receptor. J Cell Sci 123, 1716-1723.

Bitler, B. G., Menzl, I., Huerta, C. L., Sands, B., Knowlton, W., Chang, A., and Schroeder, J. A. (2009). Intracellular MUC 1 peptides inhibit cancer progression. Clin Cancer Res 15, 100-109.

Finn, R. S., Press, M. F., Dering, J., Arbushites, M. Koehler, M., Oliva, C., Williams, L. S., and Di Leo, A. (2009). Estrogen receptor, progesterone receptor, human epidermal growth factor receptor 2 (HER2), and epidermal growth factor receptor expression and benefit from lapatinib in a randomized trial of paclitaxel with lapatinib or placebo as first-line treatment in HER2-negative or unknown metastatic breast cancer. J Clin Oncol 27, 3908-3915.

Hadzisejdic, I., Mustac, E., Jonjic, N. Petkovic, M., and Grahovac, B. (2010). Nuclear EGFR in ductal invasive breast cancer: correlation with cyclin-D1 and prognosis. Mod Pathol. 2010 March; 23:392-403. Epub 2010 Jan. 8.

Hsu, S. C., and Hung, M C. (2007). Characterization of a novel tripartite nuclear localization sequence in the EGFR family. J Biol Chem 282, 10432-10440.

Kittiworakarn, J., Lecoq, A., Moine, G., That, R., Lajeunesse, E., Drevet, P, Vidaud, C., Menez, A., and Leonetti, M. (2005) HIV-1 Tat Raises an Adjuvant-free Humoral Immune Response Controlled by its Core Region and its Ability to Form Cysteine-mediated Oligomers. The Journal of Biological Chemistry 281, 3105-3115.

Lin, E. Y, Jones, J G., Li, P., Zhu, L., Whitney, K. D., Muller, W. J., and Pollard, J. W. (2003). Progression to malignancy in the polyoma middle T oncoprotein mouse breast cancer model provides a reliable model for human diseases. Am J Pathol 163, 2113-2126.

Lo, H. W., Ali-Seyed, M., Wu, Y., Bartholomeusz, G., Hsu, S. C., and Hung, M. C. (2006). Nuclear-cytoplasmic transport of EGFR involves receptor endocytosis, importin beta1 and CRM1 J Cell Biochem 98, 1570-1583.

Pintens, S., Neven, P., Drijkoningen, M., Van Belle, V., Moerman, P., Christiaens, M. R., Smeets, A., Wildiers, H., and Vanden Bempt, I (2009). Triple negative breast cancer a study from the point of view of basal CK5/6 and HER-1 J Clin Pathol 62, 624-628.

Pochampalli, M. R., Bitler, B. G., and Schroeder, J. A. (2007a). Transforming growth factor alpha dependent cancer progression is modulated by Mud. Cancer Res 67, 6591-6598.

Pochampalli, M. R., el Bejjani, R. M., and Schroeder, J. A. (2007b) MUC1 is a novel regulator of ErbB1 receptor trafficking. Oncogene 26, 1693-1701

Trivedi, P., Cuomo, L., Christensson, B., Hu, L. F., Morrone, S., Frati, L., Faggioni. A., Winberg, G., and Klein, G. (2000). Augmentation of leukocyte infiltration in murine tumors expressing B-cell derived but not nasopharyngeal carcinoma derived EBV membrane protein LMP1 J Med Virol 60, 417-424.

---

The invention claimed is:

1. A polypeptide for combinatorial inactivation of ErbB1, ErbB2, and ErbB3, said polypeptide comprising:
   a. SEQ ID NO: 3; and
   b. a protein transduction domain (PTD) for cellular entry of the polypeptide, the PTD is selected from the group consisting of PTD-4, VP22, and Antenapedia protein, wherein the PTD is N-terminal to SEQ ID NO: 3;
   wherein the polypeptide when administered in vivo is effective to inhibit tumor growth.

* * * * *